US00PP17274P2

(12) United States Plant Patent
Schoenmakers

(10) Patent No.: US PP17,274 P2
(45) Date of Patent: Dec. 12, 2006

(54) ***FITTONIA* PLANT NAMED 'WHITE ANGEL'**

(50) Latin Name: *Fittonia verschaffeltii*
Varietal Denomination: White Angel

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 11 days.

(21) Appl. No.: 11/172,359

(22) Filed: Jun. 30, 2005

(51) Int. Cl.
*A01H 5/00* (2006.01)

(52) U.S. Cl. ..... Plt./373
(58) Field of Classification Search ..... Plt./373
See application file for complete search history.

(56) References Cited

U.S. PATENT DOCUMENTS

PP4,516 P * 4/1980 Engelmann ..... Plt./373
PP4,602 P * 10/1980 Cobia ..... Plt./373

OTHER PUBLICATIONS

UPOV ROM GTITM Computer Database, GTI Jouve Retrieval Software 2005/05 Citations for 'White Angel'.*

* cited by examiner

*Primary Examiner*—Wendy Haas

(57) ABSTRACT

A new cultivar of *Fittonia* plant named 'White Angel' that is characterized by small green leaves with green and white veins.

1 Drawing Sheet

Botanical classification: *Fittonia verschaffeltii.*
Variety denomination: 'White Angel'.

BACKGROUND OF THE INVENTION

The present invention relates to a new and distinct cultivar of *Fittonia* plant botanically known as *Fittonia verschaffeltii* and hereinafter referred to by the cultivar name 'White Angel'.

The new cultivar was discovered by the inventor in a cultivated area of Haaren, The Netherlands in 2002. 'White Angel' was discovered as a naturally occurring whole plant mutation of *Fittonia verschaffeltii* 'White Anne' (not patented).

Asexual reproduction by terminal cuttings of the new cultivar 'White Angel' was first done in 2002 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia cultivar 'White Angel'.*

1. *Fittonia* 'White Angel' exhibits small leaves.
2. *Fittonia* 'White Angel' exhibits green leaves with green and white veins.

The closest comparison cultivars are *Fittonia* 'Minima' (unpatented) and *Fittonia* 'Titanic' (unpatented). The new cultivar 'White Angel' is distinguishable from 'Minima' by the following characteristics:

1. 'White Angel' has a more compact habit.

The new cultivar 'White Angel' is distinguishable from 'Titanic' by the following characteristics:

1. 'White Angel' has a faster growth rate.

The new cultivar 'White Angel' is distinguishable from the parent plant 'White Anne' by the following characteristics:

1. 'White Angel' has a more compact habit than 'White Anne'.
2. 'White Angel' has smaller leaves than 'White Anne'.
3. 'White Angel' has stronger stems than 'White Anne'.

BRIEF DESCRIPTION OF THE DRAWING

The accompanying photograph illustrates the distinguishing traits of *Fittonia* 'White Angel'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'White Angel'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'White Angel' has not been tested under all possible conditions and phenotypic differences may be observed with variations in environmental, climatic, and cultural conditions, however, without any variance in genotype.

Botanical classification: *Fittonia verschaffeltii* 'White Angel'.
Use: Ornamental.
Parentage: 'White Angel' is a naturally occurring whole plant mutation of *Fittonia* 'White Anne'.
Vigor: Moderate.
Growth rate: Moderate.
Growth habit: Broad spreading, upright.
Plant shape: Flattened globular.
Suitable container size: 8.5 cm. diameter container.
Height: Average 6.2 cm.
Width: Average 11.7 cm.
Hardiness: USDA Zone 10.
Propagation: Terminal cuttings.
Time to initiate roots: Approximately 21 days to produce roots on an initial cutting at 24 degrees Centigrade.
Time to produce a rooted cutting: Approximately 35 days to produce a rooted cutting at 24 degrees Centigrade.
Crop time: 12 weeks.
Root system: Fine and fibrous.
Stem:
*Branching habit.*—Freely branching.
*Average number of lateral branches.*—3.
*Pinching.*—Not needed.
*Lateral branch diameter.*—3 mm. in diameter.
*Lateral branch length.*—3.5 cm. in length.
*Lateral branch strength.*—Moderate.
*Stem color.*—138A.
*Pubescence.*—Dense, length 1.5 mm, color N155A.
*Internode length.*—1.3 cm. between nodes.
*Internode color.*—144B.
*Shape.*—Rounded, dull.
*Surface.*—Dull.
*Stem strength.*—Moderate.

Foliage:
*Leaf arrangement.*—Opposite.
*Compound or single.*—Single.
*Leaf shape.*—Elliptic, slightly curved.
*Leaf apex.*—Rounded to bluntly acute.
*Leaf base.*—Attenuate.
*Leaf texture.*—Glabrous, slightly rugose, prominent venation.
*Leaf length.*—Average 4.9 cm. in length.
*Leaf width.*—2 mm. in width.
*Quantity of leaves per lateral branch.*—Average 6.
*Pubescence.*—Short hairs on margins, 0.5 mm. in length, N155A.
*Leaf margin.*—Entire and slightly repand.
*Vein pattern.*—Pinnate.
*Young leaf color,* (*upper surface*).—Between 136A and 139A.
*Young leaf color,* (*lower surface*).—138A.
*Mature leaf color,* (*upper surface*).—Slightly darker than 139A.
*Mature leaf color,* (*lower surface*).—N138B.
*Vein color* (*upper surface*).—157D, darker towards base, 145A to 145B.
*Vein color* (*lower surface*).—144B to 144C.
*Leaf attachment.*—Petiolate.
*Petiole dimensions.*—Average 1.5 cm. in length, 2 mm. in diameter, 1.25 mm. in height.
*Petiole color.*—144B to 144C.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'White Angel' as described and illustrated.

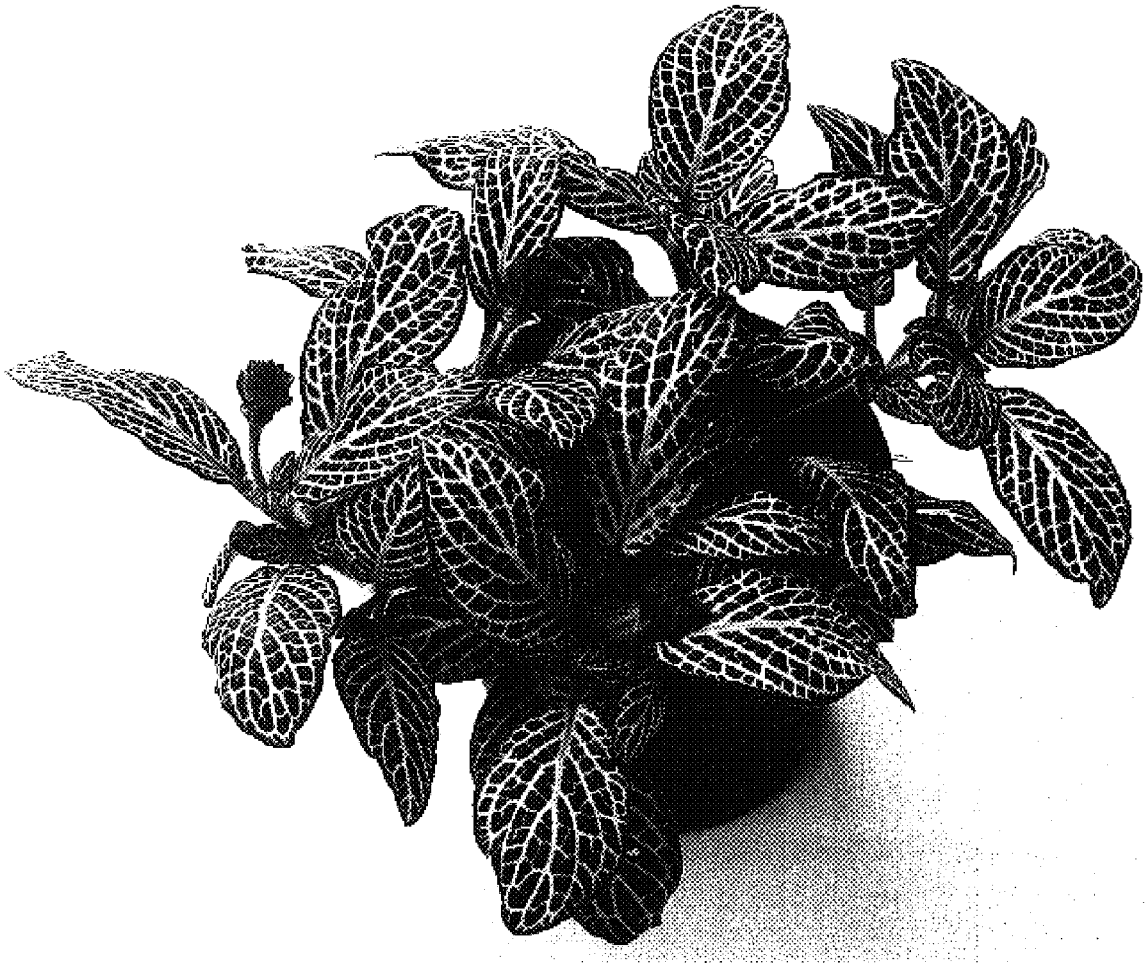

* * * * *